United States Patent

Sendelbach et al.

Patent Number: 5,380,862
Date of Patent: Jan. 10, 1995

[54] PREPARATION OF ISOMER-FREE 2,5-DICHLORO-PYRIDINE

[75] Inventors: Stefan Sendelbach, Neckarsulm; Wolfgang Weiss, Neckarhausen; Winfried Orth, Hassloch/Pflaz; Hans W. Kleffner, Battenberg/Pflaz; Albrecht Laufer, Weinheim, all of Germany

[73] Assignee: Rutgerswerke Aktiengesellschaft, Germany

[21] Appl. No.: 110,573

[22] Filed: Aug. 23, 1993

[30] Foreign Application Priority Data

Oct. 7, 1992 [DE] Germany .................. 4233708

[51] Int. Cl.⁶ .......................................... C07D 213/61
[52] U.S. Cl. ................................. 546/345; 546/290; 546/303
[58] Field of Search ................... 546/290, 303, 345

[56] References Cited

U.S. PATENT DOCUMENTS 3,244,722  4/1966  Johnston ............................ 546/303

OTHER PUBLICATIONS

Abramovitch, R. A., *The Journal of Chem Soc, Sect B, Physical Organic Chem Part I*, pp. 492–496, 1968.

Umeno, M., *Chem Abstracts*, vol. III, No. 15, 134004y, p. 746, 1989.

E. Spinner, *J. Chem Soc, Perkin Trans.*, pp. 991–995, 1966.

Min-Jen Shiao, *Synthetic Comm.*, 20(19), pp. 2917–2977, 1990.

Kikugawa, K. et al., "Studies on the Vilsmeier Haack Reactions . . . ", J. Org Chem, vol. 37, No. 2, 284–288, 1972.

Fieser, L., *Reagents for Organic Synthesis*, 286–288, 1967.

Henderson, *Organic Chemistry*, p. 10, 1970.

*Primary Examiner*—C. Warren Ivy
*Assistant Examiner*—D. Margaret M. Mach
*Attorney, Agent, or Firm*—Bierman and Muserlian

[57] ABSTRACT

A process for the preparation of isomer-free 2,5-dichloropyridine comprising alkoxylating 2-chloro-pyridine or 2-bromo-pyridine in the presence of a base at elevated temperatures, chlorinating with gaseous chlorine the alkoxylated product at ambient temperatures in an aqueous suspension in the presence of an auxiliary base, a small amount of a catalyst and optionally a small amount of an emulsifier, treating the isomer reaction mixture with a Vielsmeyer-Haack reagent, subjecting 2,5- and 2,3-dichloropyridine mixture to water vapor distillation and crystallizing the crystalline product from an alcohol-water mixture.

16 Claims, No Drawings

PREPARATION OF ISOMER-FREE 2,5-DICHLORO-PYRIDINE

Both 2,5- and 2,3-dichloropyridine constitute valuable intermediate products for the production of agrochemicals, as for instance, herbicides or insecticides. But they are also used for synthesizing pharmaceuticals, as e.g. compounds having an antidepressive or tension-releasing action. 2,5-dichloropyridine, consumed until now in relatively large amounts, is normally produced from 2-aminopyridine by a process described in U.S. Pat. No. DE 1,695,659 which is based on a dediazotizing reaction wherein the amino group, which originally served to direct the chlorination to the para-position, is based on a dediazotizing reaction wherein the amino group which originally served to direct the chlorination to the para-position is replaced by chlorine as the substituent. This substitution takes place in the presence of copper or copper chloride. The 5-chloropyridine-2-one obtained as by-product is also coverted by treating with POCl in dimethylformamide into the desired 2,5-dichloropyridine. A serious disadvantage of this process is not only the low yield of the first chlorination step of about 63%, but also the toxic properties of 5-chloro-2-aminopyridine, which even in minute traces is undesirable in pharmaceutical products, although toxicologically, it is classified as having low toxicity.

Besides these processes carried out in comparatively large volume, other methods for the production of 2,5-dichloropyridine are known, all of which, however, have considerable disadvantages. U.S. Pat. No. 3,947,457 describes a process by which 2,5-dichloropyridine is obtained from 2,3,4,5-tetrachloropyridine in 91% yield by treatment with hydrazine in ethanol in the presence of triethyleneamine. However, this process cannot be carried out on an industrial scale because of the cancerogenicity of hydrazine.

Also, two Japanese documents (JP 01/121 267 A2, JP 58/206 564 A2) describe the chlorination of 2-chloropyridine with $Cl_2$ in the presence of ferric-chloride catalysts. It is, however, a disadvantage that for carrying out these chlorination methods, high temperatures are needed and the reaction has a comparatively low selectivity. Considerable amounts of other di-, tri- and tetrachlorides are formed.

OBJECTS OF THE INVENTION

It is an object of the invention to provide an industrial method by which pure 2,5-dichloropyridine can be produced in high yields, but which does not lead to the formation of undesirable toxic by-products and does not involve the use of cancerogenic substances.

It is another object of the invention to provide the novel intermediate, 2-butoxy-5-chloro-pyridine.

These and other objects and advantages of the invention will become obvious from the following detailed description.

THE INVENTION

The novel process of the invention for the preparation of isomer-free 2,5-dichloro-pyridine comprises alkoxylating 2-chloro-pyridine or 2-bromo-pyridine in the presence of a base at elevated temperatures, chlorinating with gaseous chlorine the alkoxylated product at ambient temperatures in an aqueous suspension in the presence of an auxiliary base, a small amount of a catalyst and optionally a small amount of an emulsifier, treating the isomer reaction mixture with a Vielsmeyer-Haack reagent, subjecting 2,5- and 2,3-dichloro-pyridine mixture to water vapor distillation and crystallizing the crystalline product from an alcohol-water mixture.

The alkoxylation of 2-chloro-pyridine with an alcohol to form the corresponding 2-alkoxy-pyridine is known and subsequent chloroation thereof results in a mixture of chlorinated products including 5-chloro-2-alkoxy-pyridine from which 2-chloro-pyridines or pyridones can be formed by further reactions.

It has now been found that the chlorination of 2-alkoxypyridine can be shifted in favor of the 5-chloro product if the chlorination reaction takes place at room temperature in an aqueous medium in the presence of an auxiliary base and a catalyst. The reaction can be accelerated if small amounts of an emulsifier are added to the reaction medium and especially high yields of 5-chloro-2-alkoxypyridine are obtained if the alkoxy has 4 to 8 carbon atoms. For example, chlorination of 2-butoxypyridine yields up to 85% of 5-chloro-2-butoxypyridine, about 14% of 3-chloro-2-butoxypyridine, and less than 1% of 3,5-chloro-2-butoxypyridine are obtained for a total yield of 90% by weight.

5-chloro-2-butoxypyridine is an intermediate product for the production of the pharmaceutical intermediate, 2-hydroxy-5-chloro-pyridine, by hydrolytic splitting with an acid such as HCl, and as compared with the conventionally used methoxy or ethoxy derivatives, it offers an outstanding advantage. The butyl chloride formed in the hydrolysis with hydrochloric acid is not volatile even under reaction conditions. Costly waste air treatment is therefore unnecessary. Besides, butyl chloride which is easy to recover by distillation is a valuable, industrially usable intermediate product.

The advantage of this is that the two main products can be subjected jointly under the conditions of a Vielsmeyer-Haack reaction to chlorinating ether splitting, the reaction products being 2,5-dichloropyridine, 2,3-dichloropyridine and the respective chlorhydrocarbon such as n-butyl chloride. This means that by the use of alcohols with 4 or more carbon atoms not only is the yield of the desired chlorination products increased, but also a more ecophile process is employed as the resulting chlorhydro-carbons are not volatile at the reaction temperature.

In the further course of the process, the dichloropyridine isomer mixture can be worked up in a simple manner with a solid containing up to 96% 2,5-dichloropyridine being formed and an oil being separated in which the 2,3-dichloro-pyridine is concentrated to as much as 40%. By simple crystallization from an alcohol/water mixture, 2,5-dichloropyridine can be produced in a purity of up to 100%. 2,3-dichloropyridine, which is still contaminated inter alia with the chlorinated hydrocarbon formed, can be obtained pure in a simple manner known per se.

A special development of the process consists in that the 2-alkoxy-chloropyridine isomer mixture is taken up in a solvent and the 5-chloro isomer is precipitated as an ammonium salt by introducing a hydrohalide, the 3-isomer remaining in solution. After neutralization with a base, an isomer-pure, 5-chloro-2alkoxypyridine is obtained. Both isomers, 5-chloro-2-alkoxypyridine and the isolated 3-chloro-2- alkoxypyridine, can then be converted separately to the dichloropyridines in the above described manner.

To carry out the process, the alcohol used for the alkoxylation is added to a reactor in 2.5 to 4 times the molar quantity, based on the 2-chloropyridine to be alkoxylated, and mixed with cooling, with 1.2 to 1.7 times the molar amount of base, again based on 2-chloropyridine while the temperature is maintained at 25° to 40° C. to the extent possible. The alkoxylation reaction takes place under a nitrogen atmosphere, preferably at a temperature of about 110° C. But it is possible also to operate at reflux temperatures. Working up of the alkoxylation products is effected in the usual manner by separation of the formed alkali metal or alkaline earth metal chloride and distillation of the excess alcohol.

Examples of alkoxylation agents are all alcohols with 4 to 10 carbon atoms that are liquid at room temperature. Preferably those with 4 to 8 carbon atoms are used. They are preferably n-, i- and t-butanol, all branched and straight-chained primary, secondary and tertiary pentanols, hexanols, heptanols and octanols, provided their alcoholates and corresponding chlorides are liquid. Otherwise, the reaction temperature would have to be raised and that would lower the yield of the alkoxylation product. All alkali metal and alkaline earth hydroxides are suitable for the production of the alcoholates, but preferred are NaOH, LiOH and KOH.

For chlorinating the 2-alkoxypyridine, the latter is added to a reactor at room temperature with 10 to 20 times, preferably 15 to 19 times, the molar quantity of distilled water, up to one percent of emulsifier, up to one percent of catalyst, and about one tenth of the total amount of auxiliary base to be proportioned in, about 0.5 or 0.8 mole per mole of 2-alkoxypyridine. While stirring with the temperature being maintained, chlorine gas is introduced until the reaction is finished. During the reaction, more auxiliary base is added in portions whenever the pH value drops below 7 and the previously added auxiliary base is completely dissolved. The feeding of chlorine gas is controlled so that about 1.1 to 1.5 times the molar quantity, based on the 2-alkoxypyridine, is consumed by the end of the reaction.

The emulsifiers to be used in this reaction are those which in the presence of reactive chlorine maintain their reactivity, particularly alkyl sulfonates with 10 to 18 carbon atoms. It is of special advantage that at room temperature, the emulsifier proportion can be low. Thus as little as 0.1%, based on the total amount, may be sufficient and generally, up to 1% emulsifier is used.

Examples of auxiliary bases for the reaction are any alkali metal or alkaline earth metal oxide or hydroxide such as $Li_2O$, MgO, CaO, BaO, NaOH, KOH, LiOH, $Mg(OH)_2$, $Ca(OH)_2$, $Ba(OH)_2$, $Na_2CO_3$, $Li_2CO_3$, $MgCO_3$, $CaCO_3$, $BaCO_3$ or alkali metal or alkaline earth metal acetate. Preferably, the alkaline earth metal oxides are used, most preferably MgO.

The catalyst used in the reaction may be iodine or bromine which, like the emulsifier, can be proportioned very low. As little as about 0.1 to 1% based on the total reaction amount by weight, is sufficient for an adequate efficiency to be reached. In some cases, it is even possible to forego the addition of a catalyst altogether.

After completing the chlorination, the reaction solution is adjusted by addition of a carbonate to a pH of about 5 to 6 and the resulting phases are worked up separately, namely by distillation at 10 Torr and a boiling point of 75° C. While this does not permit separation of the isomer mixture, it is freed of by-products, emulsifiers, catalysts and chloride salts. The resulting isomer mixture consisting up to 85% 5-chloro isomer and approximately 15% 3-chloro isomer, is then chlorinated in the 2-position in a known manner, e.g. as known from Synthetic Communications, Vol. 20 (19), pgs. 2971–2977, (1990), by treatment with a Vielsmeyer-Haack reagent. The dichloropyridine isomer mixture obtained is then subjected to water vapor distillation with the formation of a solid phase and an oil.

In the solid phase is 85–95% of 2,5-dichloropyridine and small amounts of 2,3-dichloropyridine and the 2,5-isomer can be obtained by crystallization from an alcohol/water mixture in up to 100% purity.

As alcohol for this purpose, an alcohol from the group of isopropanol, n-, i-, t-butanol, a pentanol or hexanol, except cyclohexanol may be used. The 2,3-dichloropyridine contained in the separated oil can be obtained pure by the method described in the literature.

In the following examples, there are described several preferred embodiments to illustrate the invention. However, it is to be understood that the invention is not intended to be limited to the specific embodiments.

EXAMPLES

EXAMPLE 1

2-Butoxypyridine from 2-chloropyridine

Into a solution of 55 g (1,38 mole) of sodium hydroxide in 245 g of n-butanol heated to 100° C., were added dropwise over four hours 113.5 g (1 mole) of 2-chloropyridine and the mixture was stirred for about 15 hours at this temperature, then heated for 2 hours at reflux (ca. 112° C.). After cooling, precipitated sodium chloride was removed by filtering and the residue was washed with about 500 ml of n-butanol. The combined filtrates were distilled in vacuum and the first fraction to distill was a butanol-water azeotrope, then followed n-butanol and a 2-chloropyridine/n-butanol intermediate run. 2-butoxypyridine distilled last at 75° C. at 10 Torr as a colorless liquid to obtain 108 g (72%) of 2-butoxypyridine with a purity of >98%.

EXAMPLE 2

Chlorination 1000 g (6.6 mole) of 2-butoxypyridine, 2207 g (122 mole) of distilled water, 1 g of alkyl sulfonate with 13 to 18 carbon atoms/molecule, e.g. Hostapur SAS 60, 6.6 g (0.03 mole) of iodine, and about 17 g of MgO as base were placed in a 5-liter flask with a stirrer and the mixture was stirred at room temperature (23° to 25° C.). Then, chlorine gas was added until the MgO was completely dissolved and the pH value was <7. This process was repeated until a total of 176 g (4.4 mole) of MgO had been consumed. As the reaction was exothermic, the temperature had to be held below 30° C. by cooling during the entire reaction period. The total chlorine quantity was 606 g (8.5 mole). Stirring and cooling was continued for another 30 minutes after the end of the reaction, whereby excess chlorine gas was removed and secondary reactions which had caused the temperatures to rise were diminished. The pH value of the reaction mixture was about 1 and it was adjusted to about 5 to 6 by portionwise addition of sodium bicarbonate.

In a 6-liter stirring flask, a phase separation into an aqueous light yellow phase and an organic intensely yellow phase took place in about 10 minutes. The phases were separated and the organic phase was distilled under vacuum to obtain 1,110 g (90%) of product with a boiling point of 117° to 119° C. According to GC and 1H-NMR, the product was 85% by weight of 5-chloro-2-butoxy-pyridine and 15% by weight of 3-chloro-2-butoxypyridine.

The amount of chlorine added over 7 hours was 606 g (8.5 mole) for a Yield of 90%.

EXAMPLE 3

Production of 2,3- and 2,5-dichloropyridine

To 231 g (1.5 mole) of phosphorus oxychloride were added dropwise at 100° C. over 5 hours a solution of 112 g (0.6 mole) of chlorobutoxy-pyridine mixture from Example 2 in 105 g (1.5 mole) of dimethylformamide and the mixture was stirred for 20 hours at 100° C. Then, butyl chloride and phosphorus oxychloride were removed by vacuum distillation and the cooled liquid residue was hydrolyzed, cooling with 500 ml of water, and neutralizing with 270 g of 50% sodium hydroxide solution. The 2,5-dichloropyridine as well as 2,3-dichloropyridine and little n-butyl-chloride were purified by water vapor distillation and the residue was separated from the water by vacuum filtration to obtain 52 g (70%) of a mixture of 2,5-and 2,3-dichloropyridine.

EXAMPLE 4

2,5-Dichloropyridine 62 g of the mixture of Example 3 were crystallized from 200 g of an isopropanol/water mixture (15:85) to obtain 42 g of 2,5-dichloropyridine (62%, referred to the original percentage of 2,5-dichloropyridine in the starting material (85%) 80% yield with a melting point of 58° to 59° C. [den Hertog et al., Recueil trav. chim., Vol. 69 (1950), p. 673. −59° to 60° C.]

EXAMPLE 5

Isomer separation of 5-Chloro-2-butoxypyridine and 3-chloro-2-butoxypyridine 0.85 mole of dry hydrogen chloride were added to a solution of 1 mole of the chlorobutoxypyridine mixture (85% 5- and 15% 3-isomer) of Example 4 in toluene while cooling. The precipitated 5-chloro-2-butoxy-pyridine hydrochloride was recovered by filtration $^1$H-NMR [CDCl$_3$]=1.00 (t, 3H, CH$_3$), 1.55 (sext, 2H, butyl-3-CH$_2$), 1.95 (quint., 2H, butyl-2-CH$_2$), 4.62 (t, 2H, O-13 CH$_2$), 7.35 (d, 1H, pyridyl-3H), 8.20 (dd, 1H, pyridyl-4H), 8.38 (d, 1H, pyridyl-6-H), 9.20 (br s, 1 H, NH).

The hydrochloride was neutralized with sodium hydroxide solution and a yield of 133 g (referred to the total content) of 5-chloro-2-butoxypyridine were separated (85% of the theory).

Various modifications of the process of the invention may be made without departing from the spirit or scope thereof and it is to be understood that the invention is intended to be limited only as defined in the appended claims.

What we claim is:

1. A process for the preparation of isomer-free 2,5-dichloro-pyridine comprising alkoxylating at reflux 2-chloro-pyridine or 2-bromo-pyridine in the presence of an alkali metal hydroxide or alkaline earth metal hydroxide at elevated temperatures to form the 2-alkoxy-pyridine, chlorinating with gaseous chlorine the alkoxylated product at ambient temperatures in an aqueous suspension in the presence of an alkali metal or alkaline earth metal hydroxide or oxide as auxiliary bases, a small amount of a catalyst and optionally a small amount of an emulsifier where the auxiliary base is added whenever the pH drops below 7 and the previously added auxiliary base is completely dissolved to form a chloro-2-alkoxy-pyridine isomer reaction mixture, treating the isomer reaction mixture with a Vielsmeyer-Haack reagent, subjecting 2,5- and 2,3-dichloropyridine mixture to water vapor distillation and crystallizing the crystalline product from an alcohol-water mixture.

2. A process for the preparation of pure 2,5-dichloro-pyridine comprising
   a) alkoxylating 2-chloro-pyridine or 2-bromo-pyridine at elevated temperatures up to reflux in the presence of an alkali metal hydroxide or alkaline earth metal hydroxide,
   b) chlorinating with chlorine gas the resulting alkoxylated product in aqueous suspension at room temperature in the presence of an alkali metal or alkaline earth metal hydroxide or oxide as auxiliary base, a small amount of catalyst and optionally a small amount of emulsifier where the auxiliary base is added whenever the pH drops below 7 and the previously added auxiliary base is completely dissolved,
   c) distilling the resulting isomer mixture in an aromatic solvent and introducing gaseous hydrogen chloride to precipitate 2-alkoxy-5-chloro-pyridine hydrochloride,
   d) reacting the latter with a Vielsmeyer-Haack reagent,
   e) subjecting the resulting crude 2,5-dichloro-pyridine to water vapor distillation, and
   f) crystallizing the product from an alcohol-water mixture.

3. The process of claim 2 wherein the 2-alkoxy-3-chloro-pyridine left in solution after introduction of gaseous hydrogen halide and separation from the 2-alkoxy-5-Cl-pyridine
   a) is freed from the solvent by distillation,
   b) treated with a Vielsmeyer-Haack reagent,
   c) subjected to water vapor distillation, and
   d) the oil enriched with 2,3-dichloropyridine is processed to recover the product.

4. The process of claim 1 wherein the alkoxylation is effected at a temperature of <110° C.

5. The process of claim 1 wherein the auxiliary base is selected from the group consisting of Li$_2$O, MgO, CaO, BaO, NaOH, KOH, LiOH, Mg(OH)$_2$, Ca(OH)$_2$, Ba(OH)$_2$, Na$_2$CO$_3$, K$_2$CO$_3$, Li$_2$CO$_3$, MgCO$_3$, CaCO$_3$, BaCO$_3$ and alkali metal or alkaline earth metal acetate.

6. The process of claim 1 wherein iodine or bromine is used in an amount of less than 1%, based the molar quantity of the alkoxypyridine used as the catalyst.

7. The process of claim 1 wherein an emulsifier which remains reactive in the presence of chlorine is used in an amount of less than 1%, based on the amount of alkoxypyridine used.

8. The process of claim 1 wherein the emulsifier is an alkyl sulfonate of 10 to 18 carbon atoms used in an amount of less than 1%, based on the amount of alkoxypyridine used.

9. The process of claim 1 wherein the chlorination is carried out with one part of 2-alkoxy-5-chloropyridine per 2.5 to 3.5 parts of POCl$_3$ in 2 to 4 parts of DMF, based on the molar quantities.

10. The process of claim 1 wherein the crystallization is effected from a mixture of water and an alcohol selected from the group consisting of isopropanol, n-, t- or i-butanol, pentanol and hexanol.

11. The process of claim 1 wherein the alkoxylation is carried out in a primary, secondary or tertiary alcohol of 4 to 8 carbon atoms.

12. The process of claim 1 wherein the alkoxylation is carried out in n-butanol, i-butanol or sec. butanol.

13. The process of claim 1 wherein the alkoxylation is carried out in pentanol, hexanol, heptanol or octanol.

14. 5-Chloro-2-butoxypyridine.

15. A process for the preparation of isomer-free 2,5-dichloro-pyridine comprising alkoxylating at reflux 2-chloro-pyridine or 2-bromo-pyridine in the presence of an alkali metal hydroxide or alkaline earth metal hydroxide at elevated temperatures to form the 2-alkoxy-pyridine, chlorinating with gaseous chlorine the alkoxylated product at ambient temperature in an aqueous suspension in the presence of an auxiliary base, a small amount of a catalyst and optionally a small amount of an emulsifier where the auxiliary base is added whenever the pH drops below 7 and the previously added auxiliary base is completely dissolved to form an isomer reaction mixture, treating the isomer reaction mixture with a Vielsmeyer-Haack reagent, subjecting 2,5- and 2,3-dichloropyridine mixture to water vapor distillation and crystallizing the crystalline product from an alcohol-water mixture.

16. A process for the preparation of isomer-free 2,5-dichloro-pyridine comprising alkoxylating 2-chloro-pyridine or 2-bromo-pyridine in the presence of a base at elevated temperatures to form the 2-alkoxy-pyridine, chlorinating with gaseous chlorine the alkoxylated product at ambient temperature in an aqueous suspension in the presence of an alkali metal hydroxide or alkaline earth metal, hydroxide or oxide, a small amount of a catalyst and optionally a small amount of an emulsifier where the auxiliary base is added whenever the pH drops below 7 and the previously added auxiliary base is completely dissolved to form an isomer reaction mixture, treating the isomer reaction mixture with a Vielsmeyer-Haack reagent, subjecting 2,5- and 2,3-dichloropyridine mixture to water vapor distillation and crystallizing the crystalline product from an alcohol-water mixture.

* * * * *